United States Patent [19]

Klutchko et al.

[11] 4,008,252
[45] Feb. 15, 1977

[54] SUBSTITUTED-3-FORMYLCHROMONE DERIVATIVES

[75] Inventors: Sylvester Klutchko, Hackettstown, N.J.; Daniel Kaminsky, deceased, late of Parsippany, N.J., by Bernice R. Kaminsky, administratrix; Maximilian von Strandtmann, Rockaway, N.J.

[73] Assignee: Warner-Lambert Company, Morris Plains, N.J.

[22] Filed: Dec. 8, 1975

[21] Appl. No.: 638,256

Related U.S. Application Data

[60] Division of Ser. No. 480,983, June 19, 1974, abandoned, which is a continuation-in-part of Ser. No. 352,149, April 18, 1973, abandoned.

[52] U.S. Cl. .................. 260/340.5; 260/290 R; 260/345.2; 260/462 R; 260/606.5 R; 424/282
[51] Int. Cl.$^2$ ........................... C07D 317/44
[58] Field of Search ..................... 260/340.5 R

[56] References Cited

UNITED STATES PATENTS

| 3,629,290 | 12/1971 | Cairns et al. ............. 260/340.9 X |
| 3,853,921 | 12/1974 | Klutchko et al. ............ 424/283 X |
| 3,912,760 | 10/1975 | Kaminsky .................. 260/340.9 X |

FOREIGN PATENTS OR APPLICATIONS

| 769,146 | 7/1971 | Belgium |
| 777,544 | 1/1972 | Belgium |

*Primary Examiner*—Ethel G. Love
*Attorney, Agent, or Firm*—Albert H. Graddis; Frank S. Chow; Anne M. Kelly

[57] ABSTRACT

Novel 3-formylchromone derivatives are disclosed, substituted on the 5,6,7, or 8 positions by one or more of the following substituents: halogen, hydroxy, lower alkyl, lower alkoxy, lower acyl, lower acyloxy, or methylenedioxy. The corresponding 3-acetal or 3-hydrazone derivatives of the carboxaldehyde group are also disclosed. These compoounds, and pharmaceutical compositions containing these compounds are useful for the treatment of allergic conditions and for the treatment of hyperacidity.

2 Claims, No Drawings

SUBSTITUTED-3-FORMYLCHROMONE DERIVATIVES

CROSS-REFERENCE TO RELATED APPLICATION

This application is a division of U.S. Ser. No. 480,983, filed June 19, 1974, now abandoned, which is a continuation-in-part of U.S. Ser. No. 352,149, filed Apr. 18, 1973, now abandoned.

SUMMARY OF THE INVENTION

This invention relates to novel chromone derivatives having the formula I:

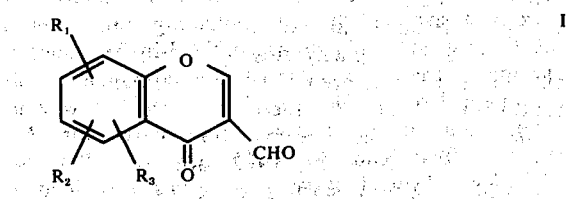

wherein $R_1$ represents halogen, hydroxy, lower alkyl, or lower alkoxy; $R_2$ represents hydrogen, or lower alkyl; $R_3$ represents hydrogen, lower acyl, or lower acyloxy; and wherein $R_1$ and $R_2$ together may form a methylenedioxy ring; and the corresponding 3-acetal or 3-hydrazone derivatives thereof. These compounds, and pharmaceutical compositions containing these compounds, are useful for the treatment of allergic conditions and for the treatment of hyperacidity.

DETAILED DESCRIPTION OF THE INVENTION

The novel compounds of this invention have the general formula I:

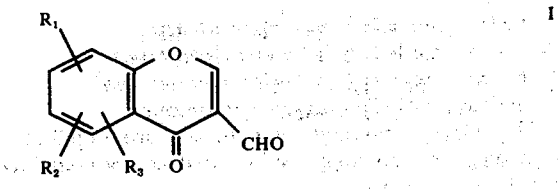

wherein $R_1$ represents halogen, hydroxy, lower alkyl, or lower alkoxy; $R_2$ represents hydrogen, or lower alkyl; $R_3$ represents hydrogen, lower acyl, or lower acyloxy; and wherein $R_1$ and $R_2$ together may form a methylenedioxy ring; and the corresponding 3-acetal or 3-hydrazone derivatives thereof. As a particularly active class of compounds, there may be mentioned those having the formula I above, wherein $R_1$ represents bromine, hydroxy, methyl, or methoxy; $R_2$ represents hydrogen or methyl, and $R_3$ represents hydrogen, acetyl or acetoxy; and wherein $R_1$ and $R_2$ together may form a methylenedioxy ring; and the corresponding 3-acetal or 3-hydrazone derivatives thereof.

In formula I above, and in all subsequent formulas, the R group substituents may be described as follows: the term "lower alkyl" is meant to include lower aliphatic hydrocarbons having 1 to 4 carbon atoms in the carbon chain, such as methyl, ethyl, propyl, isopropyl, butyl, or isobutyl. This definition for lower alkyl also applies to the lower alkyl portion of "lower alkoxy".

The term halogen is meant to include bromine, chlorine, iodine, and fluorine.

The acyl in the term "lower acyloxy" is meant to include lower alkyl carboxylic acids wherein the "lower alkyl" moiety has the above described meaning. Similarly, the term "lower acyl" is meant to include acyl groups derived from such aforementioned lower alkyl carboxylic acids.

Compounds of this invention having the general formula I above have been found to reduce histaminic responses to antigen challenge by inhibiting antibody-antigen reactions in mammals such as rats or guinea pigs upon oral or parenteral administration. When tested in accordance with the procedure of Mota, Life Sciences, 7, 465, (1963) and Ovary, Proc. Soc. Exptl. Biol. Med., 81, 584, (1952), therapeutic compositions containing the compounds of this invention are effective at dosages of 5 mg to 50 mg/kg of body weight.

Pharmaceutical compositions containing the compounds of this invention are therefore useful in the managesment of allergic reactions such as bronchial asthma. To treat bronchial asthma, a dose of 5 mg to 50 mg/kg, administered orally or parentereally is suggested; in addition, aerosol administration of lower doses may be used. The dosage may be varied depending upon severity of the condition and the weight, age and sex of the patient being treated.

In use, the compounds of this invention may be combined with a parenterally acceptable vehicle, such as a gum tragacanth saline suspension, to provide dosage forms suitable for parenteral administration; or they may be combined with pharmaceutical diluents such as lactose, cornstarch, and the like and formulated into tablet or capsule dosage forms. In order to enhance their therapeutic spectrum, the compounds of this invention may be combined with sympathomimetic agents such as isoprenaline or combined with steroids such as cortisone and its derivatives.

The compounds of this invention also exhibit antisecretory effects and are therefore useful in relieving gastric hyperacidity. Gastric hyperacidity has generally been described as a factor which contributes to peptic ulcer. The compounds of this invention, when administered to mammals in a manner as described below, have been found to inhibit the gastric secretion of hydrochloric acid and are therefore effective in reducing the resulting acidity in the stomach.

At a dosage of 20 mg/kg administered intraperitoneally, the subject compositions are effective in reducing gastric acidity in the pylorus ligated rat when tested according to the procedure of H. Shay, Gastroenterology, 5, 43, (1945).

Pharmaceutical compositions containing the compounds of this invention, are thus indicated in the management of gastric hyperacidity and the treatment of peptic ulcer resulting from such hyperacidity. For parenteral administration, the pharmaceutical composition of this invention may be administered as aqueous suspensions for intramuscular injection. These are prepared, for example, by suspending the active ingredient in sterile water and packaged in ampules so as to provide a concentration of 1,000 mg of the active ingredient per dosage unit.

Generally speaking, the dose required to effectively relieve gastric hyperacidity is within the range of 20 mg/kg of body weight of the mammal being treated. This dosage regimen may be varied depending upon the condition of the patient.

In addition to the above mentioned utilities, the compounds of this invention are useful as intermediates for the preparation of other therapeutically useful chromone derivatives, such as the corresponding carboxylic acids, esters, nitriles, oximes or acetals.

Compounds of the invention having formula I above may be prepared by one of three different procedures.

According to one process described in copending application Ser. No. 352,133, filed Apr. 18, 1973, now U.S. Pat. No. 3,912,760 compounds of the formula I are prepared by treating a compound of the formula II:

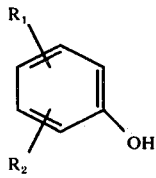

with an acid anhydride of the formula III:

$(R_4CH_2CO)_2O$                        III and boron trifluoride compound (preferably boron trifluoride etherate) to provide an intermediate of the formula IV:

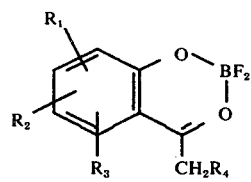

wherein $R_1$ represents hydroxy, lower alkyl, or lower alkoxy; $R_2$ represents hydrogen, or lower alkyl; $R_3$ represents hydrogen, lower acyl, or lower acyloxy, and wherein $R_1$ and $R_2$ together may form a methylenedioxy ring, and $R_4$ represents hydrogen or lower alkyl; and treating intermediate IV with a Vilsmeier reagent selected from the group consisting of phosphorus oxychloride together with dimethylformamide, and phosphorus oxychloride together with dimethylacetamide, followed by hydrolysis to yield the novel substituted 3-formylchromones of this invention.

A second method for preparing the compounds of this invention described in part by Durden, J. A. et al., in J. Org. Chem 30: 1684–1687 (1965), involves the reaction of 2-hydroxyacetophenone with acetic anhydride and boron trifluoride to provide 2,2-difluoro-4-methyl-1,3,2-benzodioxaborin. By subjecting this intermediate to reaction with the Vilsmeier reagent as taught in the novel process of co-pending application Ser. No. 352,133, filed Apr. 18, 1973, now U.S. Pat. No. 3,912,760, one obtains 3-formylchromone.

A third method by which the substituted 3-formylchromone compounds of this invention may be prepared is described in copending application Ser. No. 351,915, filed Apr. 18, 1973, now abandoned in favor of U.S. Ser. No. 480,984, filed June 19, 1974, now U.S. Pat. No. 3,886,183, and involves the oxidation of a compound of the general formula V:

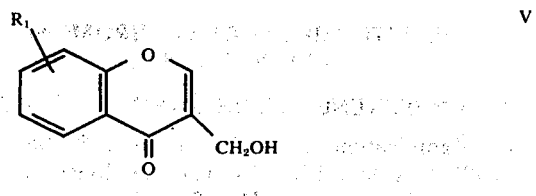

wherein $R_1$ represents halogen, lower alkyl, or lower alkoxy; with an oxidizing agent such as sodium dichromate/glacial acetic acid combination, concentrated nitric acid, or potassium persulfate, to obtain the correspondingly substituted 3-formyl chromones of this invention. Starting materials of formula V above, and various derivatives thereof containing one or more substituents on the phenyl ring of the 3-hydroxymethyl-chromone structure are described in co-pending application Ser. No. 112,765, filed Feb. 4, 1971, now abandoned; and in its continuation-in-part, Ser. No. 309,329, filed Nov. 24, 1972, now U.S. Pat. No. 3,798,240. Typical starting materials described in aforementioned Ser. Nos. 112,765 and 309,329 include:

3-(hydroxymethyl)chromone;
6-hydroxy-3-(hydroxymethyl)chromone;
6-chloro-3-(hydroxymethyl)chromone;
3-(hydroxymethyl)-6-iodochromone;
3-(hydroxymethyl)-6-methoxychromone;
6-bromo-3-(hydroxymethyl)chromone;
7-chloro-3-(hydroxymethyl)chromone;
3-(hydroxymethyl)-8-isopropylchromone;
3-(hydroxymethyl)-7-methoxychromone;
3-(hydroxymethyl)-8-methoxychromone;
8-chloro-3-(hydroxymethyl)chromone;
6-fluoro-3-(hydroxymethyl)chromone;
3-(hydroxymethyl)-6-(1,1,3,3-tetramethylbutyl)-chromone;
3-(hydroxymethyl)-8-methylchromone;
3-(hydroxymethyl)-6,8-dimethylchromone;
3-(hydroxymethyl)-6-methylchromone; and
3-(hydroxymethyl)-5-methoxychromone.

The above-mentioned compounds V are prepared by reacting correspondingly substituted compounds having the formula VI:

wherein $R_1$ is as defined above, with 2 moles of formaldehyde under basic conditions to obtain an intermediate compound having the formula VII:

wherein $R_1$ is as defined above; and treating compound VII thermally to eliminate methylsulfinic acid ($CH_3SOH$) and obtain the desired starting materials V. Compounds having the formula VI above are prepared by (A) reacting dimethylsulfoxide with sodium hydride in an inert solvent; (B) adding to reaction mixture (A) an appropriately substituted salicylic ester; (C) maintaining the reaction mixture of (B) at a temperature of up to 50° C; (D) reducing the solubility of the sodium salt reaction product of (C) by the addition of a nonpolar solvent; and (E) collecting the precipitate formed. Appropriately substituted salicylic esters used in this process are known or easily prepared by known methods. A similar process has been reported by Becker et al., in J.A.C.S. 85: 3410 (1963).

To further illustrate the practice of this invention, the following examples are included:

EXAMPLE I

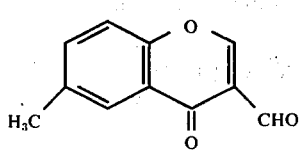

Method A — General Procedure and Preparation of 3-formyl-6-methylchromone

A solution of Vilsmeier Reagent is prepared by the dropwise addition of 153 g. (1.0 mole) of phosphorus oxychloride to ice cold dimethylformamide (365 g., 5 moles). The temperature is maintained below 10° C by use of a cooling bath. One-half mole of the appropriate boron fluoride complex is added and the mixture stirred for 15 minutes, then heated on a steam bath for 2 hours. The reaction mixture is poured onto about 3 liters of cold water. After standing at room temperature for several hours, the mixture is filtered to yield the desired substituted-3-formyl chromone derivative. Using this procedure, the following compounds are prepared: 3-formyl-6-methylchromone is prepared from 2,2-difluoro-4,6-dimethyl-1,3,2-benzodioxaborin, according to procedure A, to obtain a product having mp 171°–173° C.

Anal. Calcd. for $C_{11}H_8O_3$: C, 70.21; H, 4.29; Found: C, 69.95; H, 4.33.

EXAMPLE II

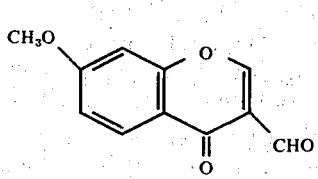

Preparation Of 7-Methoxy-3-formylchromone

7-Methoxy-3-formylchromone is prepared from 2,2-difluoro-7-methoxy-4-methyl-1,3,2-benzodioxaborin, according to procedure A of Example I, to obtain a product having mp 188°–190° C.

Anal. Calcd. for $C_{11}H_8O_4$: C, 64.70; H, 3.95; Found: C, 64.47; H, 4.09.

EXAMPLE III

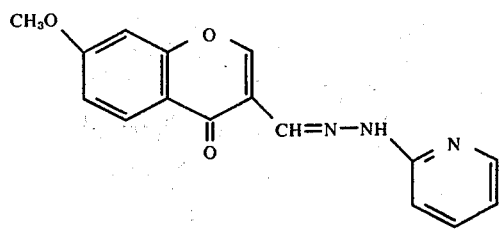

Preparation Of 7-Methoxy-4-oxo-4H-1-benzopyran-3-carboxaldehyde-2-pyridylhydrazone 7-Methoxy-4-oxo-4H-1-benzopyran-3-carboxaldehyde-2-pyridylhydrazone is prepared by reacting the product of Example II, 3-formyl-7-methoxychromone, with 2-hydrazinopyridine, to obtain a product having mp 171°–173° C.

Anal. Calcd. for $C_{16}H_{13}N_3O_3$: C, 65.08; H, 4.44; N, 14.23; Found: C, 64.95; H, 4.66; N, 14.59.

EXAMPLE IV

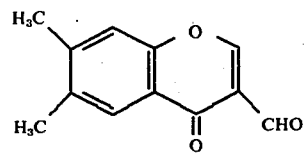

Preparation Of 3-Formyl-6,7-dimethylchromone

3-Formyl-6,7-dimethylchromone is prepared from 2,2-difluoro-4,6,7-trimethyl-1,3,2-benzodioxaborin, according to procedure A in Example I, to obtain a product having mp 154°–156° C.

Anal. Calcd. for $C_{12}H_{10}O_3$: C, 71.28; H, 4.99; Found: C, 71.11; H, 4.92.

EXAMPLE V

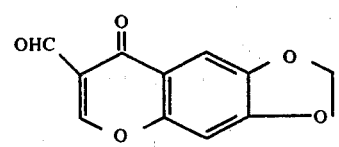

Preparation Of 3-Formyl-6,7-methylenedioxychromone

3-Formyl-6,7-methylenedioxychromone is prepared from 2,2-difluoro-4-methyl-1,3-dioxolo[4,5-g]1,3,2-benzodioxaborin, according to procedure A of Example I, to obtain a product having mp 232°–233° C.

Anal. Calcd. for $C_{11}H_6O_5$: C, 60.56; H, 2.77; Found: C, 60.80; H, 2.79.

EXAMPLE VI

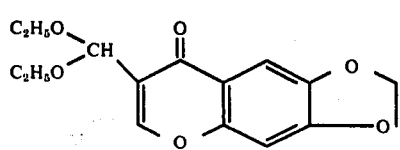

Preparation Of 8-Oxo-8H-1,3-dioxolo[4,5-g][1]benzopyran-7-carboxaldehyde diethyl acetal 8-Oxo-8H-1,3-dioxolo[4,5-g][1]benzopyran-7-carboxaldehyde diethyl acetal is prepared by reacting the product of Example VIII, 3-formyl-6,7-methylenedioxychromone, with ethanol to obtan a product having mp 123°–125° C.

Anal. Calcd. for $C_{15}H_{16}O_6$: C, 61.64; H, 5.52; O, 32.85; Found: C, 61.70; H, 5.51; O, 33.11.

EXAMPLE VII

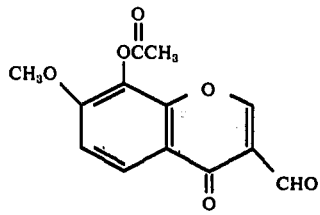

Preparation Of 8-Acetoxy-3-formyl-7-methoxychromone

8-Acetoxy-3-formyl-7-methoxychromone is prepared from 8-acetoxy-2,2-difluoro-7-methoxy-4-methyl-1,3,2-benzodioxaborin, according to procedure A of Example I, to obtain a product having mp 160°–161° C.

Anal. Calcd. for $C_{13}H_{10}O_6$: C, 59.54; H, 3.84; Found: C, 59.42; H, 3.80.

EXAMPLE VIII

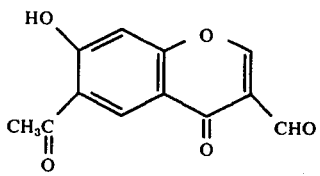

Preparation of 6-Acetyl-3-formyl-7-hydroxychromone

6-Acetyl-3-formyl-7-hydroxychromone is prepared from 6-acetyl-2,2-difluoro-7-hydroxy-4-methyl-1,3,2-benzodioxaborin, according to procedure A of Example I.

EXAMPLE IX

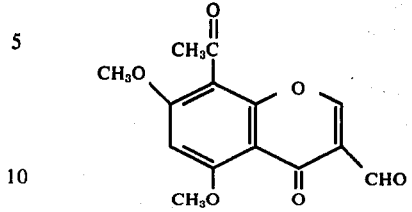

Preparation of 8-Acetyl-3-formyl-5,7-dimethoxychromone

8-Acetyl-3-formyl-5,7-dimethoxychromone is prepared from 8-acetyl-2,2-difluoro-5,7-dimethoxy-4-methyl-1,3,2-benzodioxaborin, according to procedure A of Example I.

EXAMPLE X

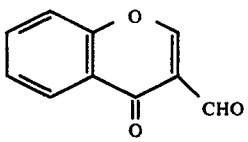

Method A — Preparation Of 3-Formylchromone

3-Formylchromone is prepared from 2,2-difluoro-4-methyl-1,3,2-benzodioxaborin, according to procedure A of Example 1, to obtain a product having mp. 149°–151° C.

Anal. Calcd. for $C_{10}H_6O_3$: C, 68.96; H, 3.47; Found: C, 69.20; H, 3.69.

[Compound prepared by another method, reported in Eiden, F. et al., Arch. der Pharm. 300: 806–810 (1967)]

EXAMPLE XI

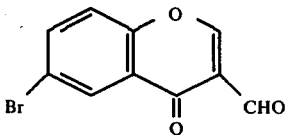

Method B — Preparation Of 6-Bromo-3-formylchromone

A warm (40° C.) solution of 29.8 g. (0.1 mole) of sodium dichromate dihydrate in 80 ml of glacial acetic acid is added over a 5-minute period to a stirred, warm (60° C.) solution of 25.5 g. (0.1 mole) of 6-bromo-3-(hydroxymethyl)chromone in 300 ml of glacial acetic acid. The temperature rises to 72° C. After one-half hour, water (1400 ml) is added and the mixture is heated at 80° C. for a few minutes. The mixture is cooled and filtered to give 13.6 g. (54%) of good quality aldehyde. Recrystallization from ethyl acetate gives pure 6-bromo-3-formylchromone having mp 186°–188° C.

Anal. Calcd for $C_{10}H_5BrO_3$: C, 47.46; H, 1.99; Br, 31.58; Found: C, 47.19; H, 1.99; Br, 31.56.

EXAMPLE XII

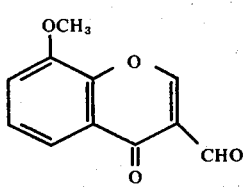

Method B — Preparation Of 3-Formyl-8-methoxychromone

A quantity of 41.2 g (0.2 mole) of 3-(hydroxymethyl)-8-methoxychromone is heated with 600 ml of glacial acetic acid to 50° C to dissolve. With stirring, a warm solution (70°) of 59.6 g (0.2 mole) of sodium dichromate dihydrate in 200 ml of glacial acetic acid is added over a period of 5 minutes, preventing the temperature from going over 80° C with cooling. After 20 minutes, about one-half of the acetic acid is distilled off at reduced pressure. Water (500 ml) is added to precipitate 13.1 g (32%) of crude aldehyde. Upon addition of more water to the filtrate, an additional 6.4 g of crude is obtained; total weight 19.4 g (48%). Purification is effected by dissolution in 150 ml of warm chloroform and filtration through a layer of silica gel; mp 171°–175° C. Recrystallization from acetonitrile gave pure aldehyde; mp 174°–176° C.

Anal. Calcd. for $C_{11}H_8O_4$: C, 64.70; H, 3.95; Found: C, 64.81; H, 3.91.

EXAMPLE XIII

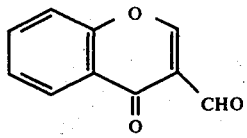

Method B — Preparation Of 3-Formylchromone

A quantity of 35.2 g. (0.2 mole) of 3-(hydroxymethyl)-chromone is dissolved in 250 ml of concentrated nitric acid with stirring at 25° C. There is no initial heat of reaction. The temperature gradually rises to 30° C over the next several minutes and is kept there for about 5 minutes with ice-acetone bath cooling. Water, 600 ml, is added to the reaction solution. The separated, pale yellow solid is filtered, washed well with water and dried to give 25 g. of crude aldehyde melting at 145°–148°.

Purification to remove a minor, slow-moving spot on thin-layer chromatography (ethylacetate-silica gel) is effected by dissolution of above 25 g. in 500 ml of methylene chloride and filtration through a silica gel column about 10 cm. long by about 5.0 cm. diameter) and washing with 500 ml methylene chloride. Concentration of the filtrate gives 20.0 g. (68%) of pure aldehyde melting at 151°–152° C.

Anal. Calcd for $C_{10}H_6O_3$: C, 68.97; H, 3.47. Found: C, 68.76; H, 3.19.

[Compound prepared by another method, reported in Eiden, F. et al., Arch. der Pharm. 300: 806 (1967)]

EXAMPLE XIV

Evaluation of Gastric Anti-ulcer Activity (in vivo)

Male rats are subjected to ligation of the gastropyloric junction. This operation causes the secretion of large quantities of gastric juice which leads to mucosol erosion in the ruminal area of the rat's stomach. The compound to be tested is given intraperitoneally (I.P.) at the time of ligation. The rats are sacrificed after 18 hours and their stomaches are removed. The efficacy of the test compound is evaluated by its ability to minimize the erosion of stomach mucosa and/or decrease the volume of acid secretions below harmful levels. Results with compounds of Examples X* and XI** are indicated in Table I below:

TABLE I

| Compound | Dose mg/kg | Route | % Decrease of Acid Volume |
|---|---|---|---|
| Ex. X | 20 | I.P. | 47.2 |
| Ex. XI | 20 | I.P. | 31.7 |

*This compound, 3-formylchromone, is also prepared in Example XIII according to Method B.
**6-Bromo-3-formylchromone

EXAMPLE XV

Anti-allergy Evaluation In The Passive Cutaneous Anaphylaxis (PCA)

Rats, passively sensitized with reogin type antibodies, are pretreated with the test compound and challenged with antigen-Evans blue mixture. After 30 minutes the animals are sacrificed and the skin containing the four sensitizing sites is removed. The activity is evaluated by the ability of the compound to minimize tissue reaction to challenge. This is indicated by the decrease in size and coloration of the areas around injection sites when compared to controls. Results with compounds of Examples X* and XI** are indicated in Table 2 below:

TABLE 2

| Compound | Dose mg/kg | Route | Inhibition of Passive Cutaneous Anaphylaxis |
|---|---|---|---|
| Ex.XI | 50 | I.P. | 51% |
| Ex.X | 100 | Per Os | 35% |

*This compound, 3-formylchromone, is also prepared in Example XIII according to Method B.
**6-Bromo-3-formylchromone Human atopic allergy has been shown to be due to a specific class of antibody (IgE), which is heat labile and fixes for long times in the skin after passive transfer with the serum of sensitive individuals. A similar type of antibody is found in the rat. This antibody is non-precipitating. Therefore, it is a most unique type. This antibody releases histamine and serotonin from mast cells in the rat as it does in the human. Thus, any drug which interferes with the passive cutaneous anaphylaxis reaction in the rat becomes of interest for treatment of human allergy.

EXAMPLE XVI
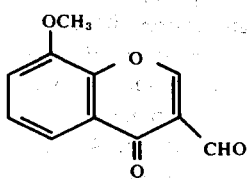
Preparation of 3-Formyl-8-methoxychromone
8-Methoxy-3-formyl chromone is prepared from 2,2-difluoro-8-methoxy-4-methyl-1,3,2-dioxaborin, according to procedure A of Example I, to obtain a product having a melting point of 174°–176° C.
Anal. Calcd. for $C_{11}H_8O_4$: C, 64.70; H, 3.95; Found: C, 64.81; H, 3.91.
We claim:
1. 3-Formyl-6,7-methylenedioxychromone.
2. 8-Oxo-8H-1,3-dioxolo[4,5g][1]benzopyran-7-carboxaldehyde diethyl acetal.
* * * * *